United States Patent
Kim et al.

(10) Patent No.: US 8,623,425 B2
(45) Date of Patent: Jan. 7, 2014

(54) METHOD FOR PREPARING EXTRACT FRACTON REINFORCED WITH GINSENOSIDES RG1 OR RB1 FROM GINSENG

(75) Inventors: Yeong-Eun Kim, Seoul (KR); Doo-Kyung Kim, Seoul (KR); Yong-Ki Seo, Seoul (KR); Jin-Hee Lee, Seoul (KR)

(73) Assignee: CJ Chieljedang Corp., Seoul (KR)

( * ) Notice: Subject to any disclaimer, the term of this patent is extended or adjusted under 35 U.S.C. 154(b) by 155 days.

(21) Appl. No.: 13/127,371

(22) PCT Filed: Oct. 30, 2009

(86) PCT No.: PCT/KR2009/006311
§ 371 (c)(1),
(2), (4) Date: Jul. 13, 2011

(87) PCT Pub. No.: WO2010/053271
PCT Pub. Date: May 14, 2010

(65) Prior Publication Data
US 2011/0268823 A1 Nov. 3, 2011

(30) Foreign Application Priority Data
Nov. 4, 2008 (KR) .......................... 10-2008-0109038

(51) Int. Cl.
*A61K 36/00* (2006.01)
*A61K 36/254* (2006.01)

(52) U.S. Cl.
USPC .......................................... 424/725; 424/728

(58) Field of Classification Search
None
See application file for complete search history.

(56) References Cited

U.S. PATENT DOCUMENTS

2010/0056470 A1 * 3/2010 Taylor et al. .................... 514/54

FOREIGN PATENT DOCUMENTS

KR 2001010397 A * 2/2001

OTHER PUBLICATIONS

DW 2005-180377, Feb. 2005, US or DWPI 2005, Guo et al.*
Viable Herbal Solution (the cited website of http:web/archive.org/web/20000124113842/http://viable-herba.com/herbology/herbs42, copyrighted 1996-2000).*

* cited by examiner

*Primary Examiner* — Terry A McKelvey
*Assistant Examiner* — Randall Winston
(74) *Attorney, Agent, or Firm* — Porzio, Bromberg & Newman, P.C.

(57) ABSTRACT

The present invention provides a method for preparing an extract fraction reinforced with ginsenoside Rg1 or Rb1 from *ginseng*. The method for preparing an extract fraction reinforced with ginsenoside Rg1 comprises the steps of: concentrating an alcohol extract of *ginseng* and then adsorbing the extract diluted in water by adding the extract to an adsorption resin; passing distilled water through the adsorption resin, then eluting and removing unadsorbed ingredients; and adding 30 to 40 v/v % alcohol to the adsorption resin to obtain an eluate. The method for preparing an extract fraction reinforced with ginsenoside Rb1 comprises the steps of: concentrating an alcohol extract of *ginseng* and then adsorbing the extract diluted in water by adding the extract to an adsorption resin; passing distilled water through the adsorption resin, then eluting and removing unadsorbed ingredients; and adding 50 to 80 v/v % alcohol to the adsorption resin and then eluting.

6 Claims, 3 Drawing Sheets

METHOD FOR PREPARING EXTRACT FRACTON REINFORCED WITH GINSENOSIDES RG1 OR RB1 FROM GINSENG

CROSS REFERENCE TO RELATED APPLICATION

This is a National Stage of International Application No. PCT/KR2009/006311, filed Oct. 30, 2009, which claims the benefit of Application No. 10-2008-0109038, filed in Korea on Nov. 4, 2008, the disclosures of which Applications are incorporated by reference herein.

TECHNICAL FIELD

The present invention relates to a method for preparing an extract fraction reinforced with specific saponin components from *ginseng*. More particularly, the present invention relates to a method for preparing an extract fraction reinforced with ginsenoside Rg1 known to have anti-fatigue functions OR ginsenoside Rb1 known to have sedative activity, among saponin components of *ginseng*.

BACKGROUND ART

*Panax ginseng* C. A. Mayer (hereinafter, abbreviate to '*ginseng*') is a generic *ginseng* plant of the Arliaceae family. *Panax ginseng* has been used for medicinal purposes in China since B.C. and has been employed for medicinal purposes or as a trade item in Korea since the era of the Three Kingdoms. *Panax ginseng* is now widely used for preparation of oriental medicines or health supplements used for a variety of applications.

*Ginseng* generally includes about 3 to 6% of saponin-like materials called ginsenosides as species-specific ingredients and the ginsenosides are major physiological active materials and may be classified into panaxadiol (PD), panaxatriol (PT) and oleanane based ginsenosides. About 33 species of ginsenosides have recently been reported.

PD based saponin and PT based saponin have different functions in vivo. PD based saponin including ginsenoside Rb1 as a representative example, is known to exhibit inhibitory action on the central nervous system, in turn accomplishing tranquilization, neuroleptic, analgesic, anti-convulsive and/or hypotensive effects, influence upon papaverine content, or the like. On the other hand, PT based saponin including ginsenoside Rg1 as a representative example, is known to excitedly react to the central nervous system, thus exhibiting anti-fatigue activity. Therefore, it is assumed that, if saponin components in *ginseng* having opposing activities are separated or reinforced, pharmacological activity of *ginseng* may be more efficiently attained. However, most recent studies into ginsenosides are directed to a method for increasing contents of trace ingredients present in *ginseng* (U.S. Pat. No. 7,371,416), use of ginsenosides for treatment of particular diseases (WO 01/056585), or the like. However, research and investigations into techniques to improve efficacies of ginsenosides Rg1 and Rb1 showing opposing activities, respectively, have not been sufficient.

Korean Patent No. 620,107 discloses a process for production of ginsenoside Rg2 as a specific component of *ginseng* saponin by treating a water extract or an alcohol extract of *ginseng* using lactic acid. Korean Patents Nos. 517,128 and 192,678 disclose variation in yield of saponin depending upon alcohol concentration or extraction temperature in consideration of thermal stability when the saponin is extracted from *ginseng*. However, all of these techniques adopt petroleum ether as an extraction solvent, thus being unsuitable for foods or medical use. In addition, the foregoing arts neither disclosed nor suggested methods for preparing an extract fraction reinforced with ginsenoside Rg1 or Rb1.

Moreover, although Korean Patent No. 0,444,394 describes a method for preparation of an extract having high saponin content through adsorption using an adsorption resin, a process of obtaining an extract fraction reinforced with specific saponin components is not disclosed or suggested therein.

DISCLOSURE

Technical Problem

PD based saponin and PT based saponin present in *ginseng* generally show opposing activities. Therefore, according to a relative ratio of PD based saponin to PT based saponin, the *ginseng* may express different activities in vivo. Also, with regard to a composition including a *ginseng* extract, there are disadvantages such that: different activities may be imparted depending upon the ratio of ginsenoside Rb1 to Rg1; and, due to opposing activities of ginsenosides Rb1 and Rg1, effects of respective saponin components obtained from a *ginseng* extract may not be efficiently attained. Furthermore, health drinks usually consumed by normal healthy individuals without particular diseases requiring professional management of medical personnel, entail a problem such that some ingredients having undesirable effects may be taken without consciousness.

Therefore, in order to overcome disadvantages of the *ginseng* saponin extract described above, the present inventors have extensively studied a method for preparation of *ginseng* saponin extract fractions having high ratio of specific saponin components (Rb1 or Rg1) of *ginseng* as well as increased content thereof and, as a result, have developed a method of sufficiently extracting saponin from *ginseng* and a method of obtaining a fraction reinforced with specific saponin components (Rb1 or Rg1) from the foregoing, thereby completing the present invention.

Accordingly, an object of the present invention is to provide a method for preparing an extract fraction reinforced with ginsenoside Rg1 or Rb1 from *ginseng*.

Another object of the present invention is to provide a functional beverage composition with reinforced anti-fatigue effects of *ginseng* saponin, including an extract fraction reinforced with ginsenoside Rg1 obtained from *ginseng*.

Still another object of the present invention is to provide a functional beverage composition with reinforced sedative activity of *ginseng* saponin, including an extract fraction reinforced with gensenoside Rb1 obtained from *ginseng*.

Technical Solution

In order to achieve the objects described above, the present invention provides a method for preparing an extract fraction reinforced with ginsenoside Rg1 from *ginseng*, which includes:

concentrating an alcohol extract of *ginseng*, diluting the concentrated extract in distilled water, and then, adding the diluted extract to an adsorption resin in order to adsorb the extract to the adsorption resin;

passing distilled water through the adsorption resin and then eluting and removing unadsorbed ingredients; and adding 30 to 40 v/v % alcohol to the adsorption resin to obtain an eluate.

The present invention also provides a method for preparing an extract fraction reinforced with ginsenoside Rb1 from *ginseng*, which includes:

concentrating an alcohol extract of *ginseng*, diluting the concentrated extract in distilled water and then adding the diluted extract to an adsorption resin in order to adsorb the extract to the adsorption resin;

passing distilled water through the adsorption resin and then eluting and removing unadsorbed ingredients; and adding 50 to 80 v/v % alcohol to the adsorption resin to obtain an eluate.

The extract fraction prepared according to the present invention, which is reinforced with ginsenoside Rg1 or Rb1, may be added to a functional drink as an active ingredient.

Accordingly, the present invention may provide a functional drink composition having reinforced anti-fatigue effects of *ginseng* saponin, which includes an extract fraction reinforced with ginsenoside Rg1 prepared by the preparation method described above.

Alternatively, the present invention may also provide a functional drink composition having reinforced sedative activity of *ginseng* saponin, which includes an extract fraction reinforced with ginsenoside Rb1 prepared by the preparation method described above.

Hereinafter, the present invention will be described in detail.

The present inventors have found that, after removing non-saponin components from an alcohol extract of *ginseng* using an adsorption resin, an extract reinforced with ginsenoside Rg1 may be obtained through elution using 30 to 40 v/v % alcohol, while an extract reinforced with gensenoside Rb1 may be obtained through elution using 50 to 80 v/v % alcohol. As a result, a *ginseng* extract reinforced with ginsenoside Rg1 or Rb1 was obtained.

Accordingly, in an aspect of the present invention, there is provided a method for preparing an extract fraction reinforced with ginsenoside Rg1 from *ginseng*, comprising:

concentrating an alcohol extract of *ginseng*, diluting the concentrated extract in distilled water and then adding the diluted extract to an adsorption resin to adsorb the extract to the adsorption resin;

passing distilled water through the adsorption resin and then eluting and removing unadsorbed ingredients; and adding 30 to 40 v/v % alcohol to the adsorption resin to obtain an eluate.

In another aspect of the present invention, there is provided a method for preparing an extract fraction reinforced with ginsenoside Rb1 from *ginseng*, comprising:

concentrating an alcohol extract of *ginseng*, diluting the concentrated extract in distilled water and then adding the diluted extract to an adsorption resin to adsorb the extract to the adsorption resin;

passing distilled water through the adsorption resin and then eluting and removing unadsorbed ingredients; and adding 50 to 80 v/v % alcohol to the adsorption resin to obtain an eluate.

The alcohol extract of *ginseng* may include any extract obtained by treating *ginseng* with alcohol, preferably, an extract having relatively high contents of ginsenosides Rg1 and Rb1. The extract having relatively high contents of ginsenosides Rg1 and Rb1 may be obtained by adding 60 to 80% alcohol to *ginseng* and agitating the mixture at 40 to 80° C. for 24 to 36 hours to obtain an extract. As a result of extensive studies by the present inventors, the foregoing method has been developed and may be utilized as an extraction process yielding high concentrations of ginsenosides Rg1 and Rb1. If the extraction temperature exceeds 80° C., thermal stability of ginsenosides Rg1 and Rb1 is reduced, causing a decrease in contents of ginsenosides Rg1 and Rb1. On the other hand, when the extraction temperature is less than 40° C., extraction efficiency may be deteriorated. When extraction time exceeds the above range and too long, stability of ginsenosides and/or economic advantages may be reduced. On the other hand, if extraction time is too short, extraction efficiency may be deteriorated. More preferably, an alcohol extract is obtained by adding 65 to 75 v/v % alcohol to *ginseng* and agitating the same at 65 to 75° C. for 24 to 36 hours to conduct extraction. Most preferably, an alcohol extract is obtained by adding 70 v/v % alcohol to *ginseng* and agitating the same at 70° C. for 24 hours to perform extraction. The extract used herein may be prepared by repeating extraction at least three times and mixing the resultant extracts.

Then, the obtained alcohol extract of *ginseng* is subjected to heating and concentration. In this regard, concentration may be conducted to reach a range of 70 to 90 brix, most preferably, to about 80 brix.

Next, after adding water to the concentrated alcohol extract to dilute the extract, the diluted extract may be introduced into an adsorption resin to be adsorbed thereto. Dilution extent with water is not particularly limited, provided that a concentrate of the alcohol extract may react with overall adsorption resin to allow saponin to be adsorbed thereto. Preferably, about 4 to 6 fold water and, more preferably, about 5 fold water the weight of the concentrated extract may be added to the concentrated extract to dilute the same. The adsorption resin may be Diaion HP-20 (Mitsubishi, Japan) and used in a packed column form to implement adsorption and fractionation.

Following this, after passing distilled water through the adsorption resin, a process of eluting and removing unadsorbed ingredients may be executed. According to this process, other components present in the alcohol extract of *ginseng* except for saponin may be eluted and removed. An amount of distilled water used to remove unadsorbed components is determined such that non-saponin components can be sufficiently eluted and removed, without being particularly limited. For instance, distilled water in an amount of about 5 times or more the capacity of the adsorption resin may be used. Preferably, additional non-saponin components may be eluted and removed by adding about 20 v/v % alcohol.

When non-saponin components are removed from the adsorption resin, saponin may be eluted using alcohol at different concentrations to thereby yield a saponin fraction. For ginsenoside Rg1, using 30 to 40 v/v % alcohol may elute the adsorption resin, in turn yielding an extract fraction reinforced with ginsenoside Rg1. Likewise, for ginsenoside Rb1, using 50 to 80 v/v % alcohol may elute the adsorption resin, in turn yielding an extract fraction reinforced with ginsenoside Rb1. The extract fraction reinforced with ginsenoside Rg1 may have a relative ratio of ginsenoside Rg1 to ginsenoside Rb1 of at least 0.5. On the other hand, the extract fraction reinforced with ginsenoside Rb1 may have a relative ratio of ginsenoside Rb1 to ginsenoside Rg1 of at least 2.

The *ginseng* used to prepare the *ginseng* extract described above may include any one containing saponin Rb1 or Rg1, for example, selected from a group consisting of white *ginseng*, undried *ginseng*, red *ginseng*, Tae-guk *ginseng*, black *ginseng*, puffing *ginseng* or enzyme-treated *ginseng*, or concentrates thereof.

Advantageous Effects

As apparent from the foregoing description, according to the method of the present invention, an extract fraction having reinforced ratio of ginsenoside Rg1 to ginsenoside Rb1, as well as increased contents thereof, may be prepared from saponin components of *ginseng*. Moreover, a functional food reinforced with saponin components of *ginseng* prepared by the method according to the present invention, may be provided.

BRIEF DESCRIPTION OF THE DRAWINGS

The above and other objects, features and other advantages of the present invention will be more clearly understood from the following detailed description, taken in conjunction with the accompanying drawings, in which.

MODE FOR INVENTION

Figure 1:
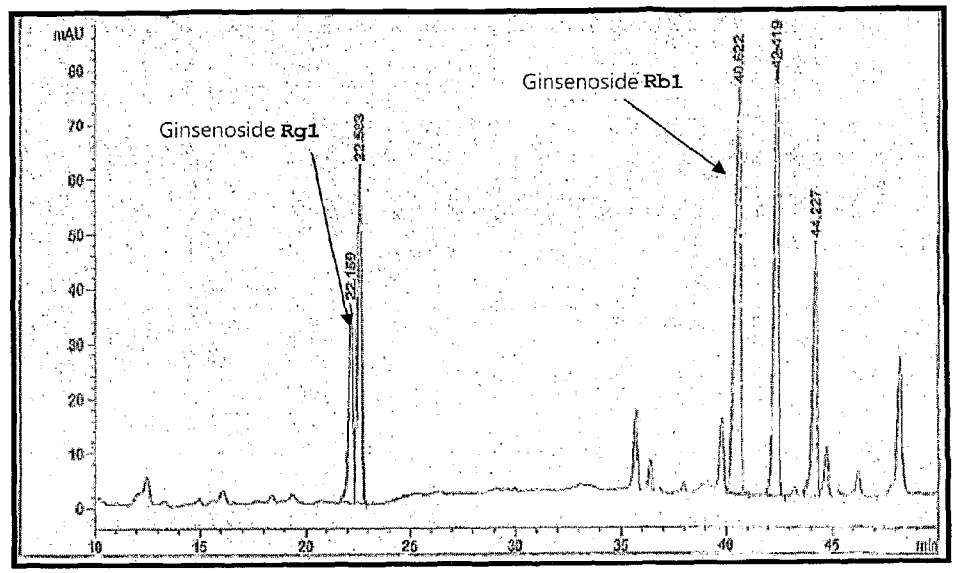
FIG. 1 is an HPLC chromatogram of an alcohol extract obtained by extracting tail *ginseng* at 70° C. for 24 hours using 70 v/v % alcohol.
Figure 2:
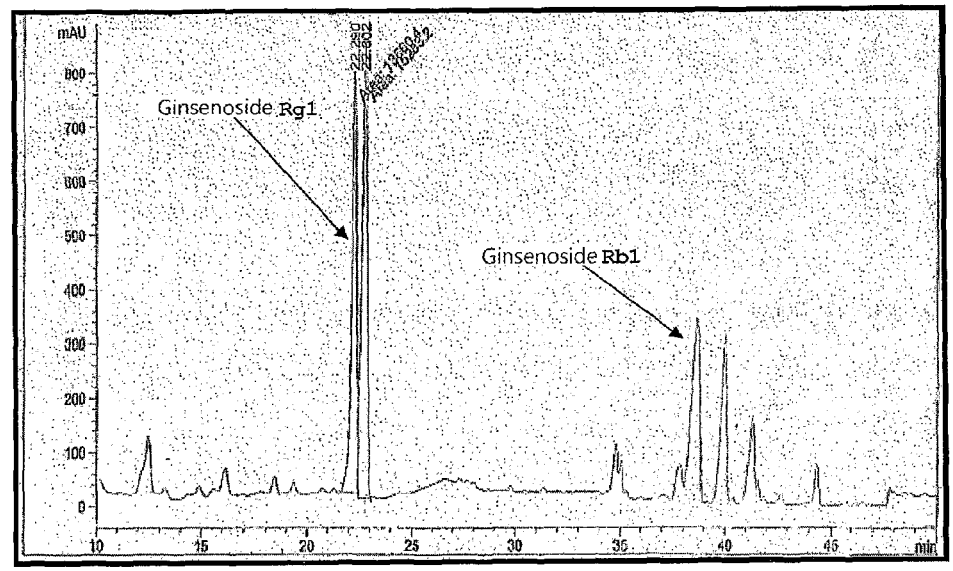
FIG. 2 is an HPLC chromatogram of a fraction reinforced with ginsenoside Rg1, which is obtained by extracting tail *ginseng* at 70° C. for 24 hours using 70 v/v % alcohol to obtain an alcohol extract, adsorbing the alcohol extract to Diaion HP-20 adsorption resin and eluting the adsorbed extract using 30 to 40 v/v % alcohol.
Figure 3:
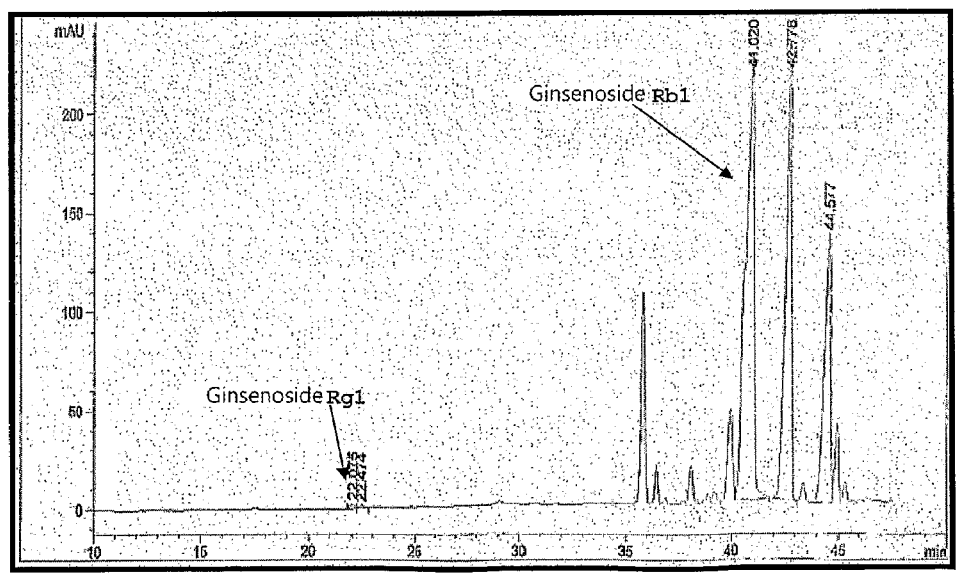
FIG. 3 is an HPLC chromatogram of a fraction reinforced with ginosenoside Rb1, which is obtained by extracting tail *ginseng* at 70° C. for 24 hours using 70 v/v % alcohol to obtain an alcohol extract, adsorbing the alcohol extract to Diaion HP-20 adsorption resin and eluting the adsorbed extract using 50 to 80 v/v % alcohol.
Figure 4:
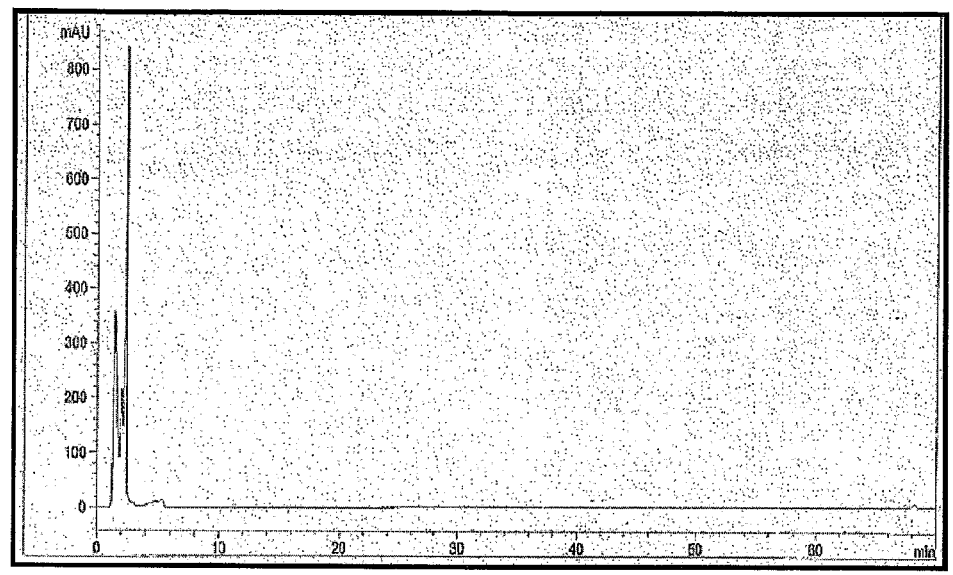
FIG. 4 is an HPLC chromatogram of a fraction obtained by extracting tail *ginseng* at 70° C. for 24 hours using 70 v/v % alcohol to obtain an alcohol extract, adsorbing the alcohol extract to Diaion HP-20 adsorption resin and eluting the adsorbed extract using 10 to 20 v/v % alcohol.
Figure 5:
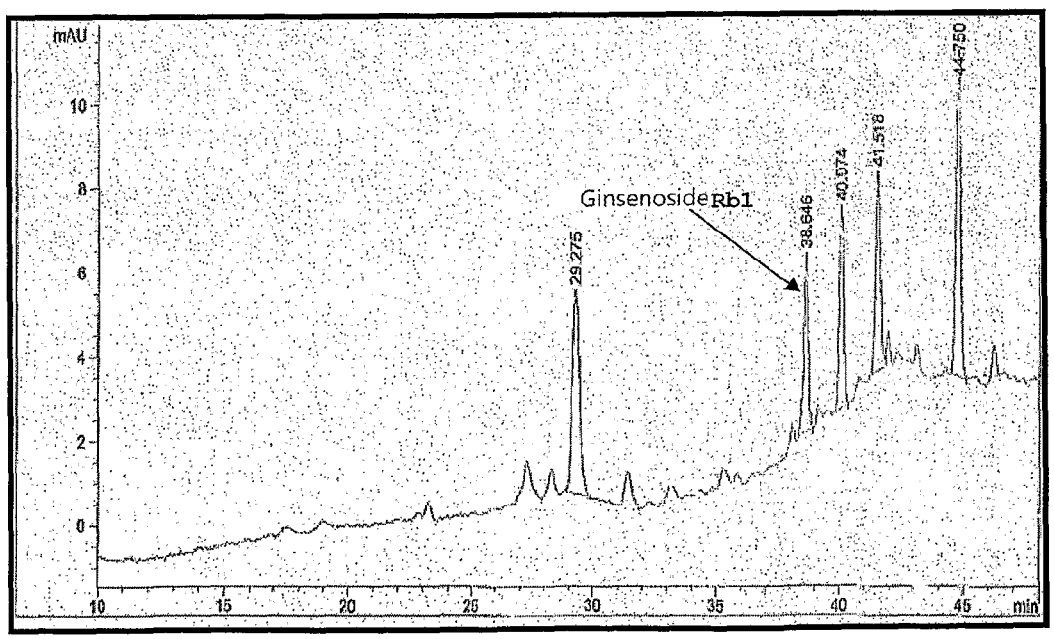
FIG. 5 is an HPLC chromatogram of a fraction obtained by extracting tail *ginseng* at 70° C. for 24 hours using 70 v/v % alcohol to obtain an alcohol extract, adsorbing the alcohol extract to Diaion HP-20 adsorption resin and eluting the adsorbed extract using 80 to 100 v/v % alcohol.

Hereinafter, preferred embodiments and examples of the present invention will be described in detail. However, these examples are given for the purpose of illustration and are not intended to limit the invention.

Experimental Example 1

Preparation of Alcohol Extract of *Ginseng*

After adding about 15 fold (that is, 15 kg) 70 (v/v) % alcohol to 1 kg of dried tail *ginseng*, the solution was extracted three times at 70° C. for 24 hours each time, followed by filtration. Alternatively, using 60% and 80% alcohol, respectively, alcohol extracts of *ginseng* were prepared by the same procedures as described above.

For each of the prepared alcohol extracts obtained by the foregoing methods, contents of ginsenosides Rg1 and Rb1 were measured using HPLC. Measured results are shown in the following Table 1.

TABLE 1

| Extraction solvent | Rg1 (mg/g) | Rb1 (mg/g) | Sum of contents of specific ginsenosides containing Rg1 and Rb1 (Rc, Rd, Re, Rb2) (mg/g) | Yield of extract relative to raw material (%) |
|---|---|---|---|---|
| 50 v/v % alcohol | 5.3 | 14.5 | 62.6 | 50 |
| 60 v/v % alcohol | 6.9 | 20.97 | 71.1 | 45 |
| 70 v/v % alcohol | 6.8 | 20.18 | 72.5 | 45 |
| 80 v/v % alcohol | 6.38 | 18.02 | 63.9 | 34 |
| 90 v/v % alcohol | 6.21 | 16.45 | 62.1 | 25 |

As apparent from the results, it was found that extracts obtained using 60 to 80 v/v % alcohol generally have high total content of ginsenosides Rg1 and Rb1, especially, when using 60 to 70 v/v % alcohol, the extract has the highest total content of ginsenosides Rg1 and Rb1.

Experimental Example 2

Preparation of *Ginseng* Extract Using 70 v/v % Alcohol

An alcohol extract of *ginseng* was prepared by the same procedures as described in Example 1, except that the alcohol concentration was set to 70 v/v % and the alcohol extract of *ginseng* was prepared while varying extraction conditions as shown in the following Table 2. Then, contents of ginsenosides Rg1 and Rb1 were measured through HPLC. Measured results are shown in Table 2.

TABLE 2

| Extraction conditions | Rg1 (mg/g) | Rb1 (mg/g) |
|---|---|---|
| 40° C.-3 hr | 6.023 | 9.928 |
| 40° C.-6 hr | 5.976 | 10.182 |
| 40° C.-10 hr | 6.204 | 10.799 |
| 40° C.-24 hr | 6.329 | 11.572 |
| 50° C.-3 hr | 6.136 | 10.698 |
| 50° C.-6 hr | 6.012 | 10.881 |
| 50° C.-10 hr | 6.068 | 11.404 |
| 50° C.-24 hr | 6.454 | 13.607 |
| 60° C.-3 hr | 6.014 | 10.852 |
| 60° C.-6 hr | 6.064 | 11.718 |
| 60° C.-10 hr | 6.054 | 12.744 |
| 60° C.-24 hr | 6.622 | 16.588 |
| 70° C.-3 hr | 6.118 | 11.098 |
| 70° C.-6 hr | 6.500 | 13.001 |
| 70° C.-10 hr | 6.581 | 16.127 |
| 70° C.-24 hr | 6.845 | 20.186 |
| 70° C.-30 hr | 6.751 | 20.904 |
| 70° C.-36 hr | 6.650 | 21.405 |
| 80° C.-3 hr | 6.015 | 14.957 |
| 80° C.-6 hr | 6.040 | 15.598 |
| 80° C.-10 hr | 6.176 | 17.254 |
| 80° C.-24 hr | 5.773 | 17.841 |
| 80° C.-30 hr | 5.415 | 16.776 |
| 80° C.-36 hr | 5.209 | 15.836 |

According to results of the foregoing experiments, it was confirmed that, if extraction is performed using 70 v/v % alcohol, contents of ginsenosides Rg1 and Rb1 vary slightly depending upon temperature conditions and, especially, Rb1 content is noticeably increased at 70° C. In addition, it was found that a total content of ginsenosides Rg1 and Rb1 is the highest at 70° C.

With regard to treatment time, it was found that, when treating for 24 hours or more, contents of ginsenosides Rg1 and Rb1 are remarkably increased. Although, in the case of treating at 80° C., the contents of ginsenosides Rg1 and Rb1 are decreased as treatment time increases, this may seem to be due to temperature instability.

It can be seen that an alcohol extract of *ginseng* is preferably prepared through treatment at 70° C. for 24 hours and HPLC results of the alcohol extract obtained through treatment at 70° C. for 24 hours are shown in FIG. 1.

Example 1

Process for Adsorption of Diaion HP-20 Adsorption Resin

The alcohol extract of *ginseng* obtained through extraction at 70° C. for 24 hours in Experimental Example 1, was heated and concentrated to 80 brix. Then, after adding water in an amount of 5 times the weight of the formed concentrate to sufficiently dilute the concentrate, the diluted extract was passed through Diaion HP-20 adsorption resin, thus enabling a saponin component to be adsorbed to the resin. Next, unadsorbed ingredients were removed by continuously flowing distilled water in an amount of about 5 times the capacity of the resin through the adsorption resin.

Following this, after passing 20 v/v % alcohol in an amount of about 5 times the capacity of the resin through the adsorption resin to remove non-saponin components, an alcohol concentration was regulated to obtain a desired ginsenoside fraction. By using alcohol, elution began at an alcohol concentration of 30 v/v % and continued until the alcohol concentration reached 40 v/v %, resulting in a fraction reinforced with ginsenoside Rg1. Alternatively, elution using alcohol began at an alcohol concentration of 50 v/v % and continued until the alcohol concentration reached 80 v/v %, in turn obtaining a fraction reinforced with ginsenoside Rb1. From these fractions, contents of ginsenosides Rg1 and Rb1 were respectively measured through HPLC. The measurement results are shown in Tables 3 and 4.

In addition, after using 30 to 40 v/v %, 50 to 80 v/v %, 10 to 20 v/v %, and 80 to 100 v/v % alcohol, respectively, to conduct elution, contents of ginsenosides were measured through HPLC. The measurement results are shown in FIGS. 2, 3, 4 and 5. From results shown in FIGS. 2 to 5, it can be seen that a fraction reinforced with ginsenoside Rg1 may be obtained by elution using 30 to 40 v/v % alcohol, while yielding a fraction reinforced with ginsenoside Rb1 when elution is performed using 50 to 80 v/v % alcohol.

TABLE 3

|  | Rg1 content |
|---|---|
| Content of ginsenoside in *ginseng* extract | 0.7 wt. % |
| Ginsenoside Rg1 reinforced fraction | 12 wt. % or more |

TABLE 4

|  | Rb1 content |
|---|---|
| Content of ginsenoside in *ginseng* extract | 2.0 wt. % |
| Ginsenoside Rb1 reinforced fraction | 18 wt. % or more |

As understood from the foregoing results, an extract fraction reinforced with ginsenoside Rg1 or Rb1 may be obtained by elution using an adsorption resin.

The invention claimed is:

1. A method for preparing an extract fraction reinforced with ginsenoside Rg1 relative to ginsenoside Rb1 from *ginseng*, comprising:
   preparing an alcohol extract of *ginseng* by adding 60 to 80 v/v % alcohol to *ginseng* and agitating the mixture at 65 to 75° C. for 24 to 36 hours;
   concentrating the alcohol extract of *ginseng*, diluting the concentrated extract in distilled water, and then, adding the diluted extract to an adsorption resin in order to adsorb the extract to the adsorption resin;
   passing distilled water through the adsorption resin and then eluting and removing unadsorbed ingredients; and
   adding 30 to 40 v/v % alcohol to the adsorption resin to obtain an eluate.

2. A method for preparing an extract fraction reinforced with ginsenoside Rb1 relative to ginsenoside Rg1 from *ginseng*, comprising:
   preparing an alcohol extract of *ginseng* by adding 60 to 80 v/v % alcohol to *ginseng* and agitating the mixture at 65 to 75° C. for 24 to 36 hours;
   concentrating the alcohol extract of *ginseng*, diluting the concentrated extract in distilled water, and then, adding the diluted extract to an adsorption resin in order to adsorb the extract to the adsorption resin;
   passing distilled water through the adsorption resin and then eluting and removing unadsorbed ingredients; and
   adding 50 to 80 v/v % alcohol to the adsorption resin to obtain an eluate.

3. The method according to claim 1, wherein the alcohol extract of *ginseng* is concentrated to 70 to 90 brix.

4. The method according to claim 1, wherein the adsorption resin is Diaion HP-20.

5. The method according to claim 2, wherein the alcohol extract of *ginseng* is concentrated to 70 to 90 brix.

6. The method according to claim 2, wherein the adsorption resin is Diaion HP-20.

* * * * *